United States Patent
Ono

(10) Patent No.: US 11,039,733 B2
(45) Date of Patent: Jun. 22, 2021

(54) IMAGE PICKUP APPARATUS AND ENDOSCOPE SYSTEM

(71) Applicant: OLYMPUS CORPORATION, Tokyo (JP)

(72) Inventor: Makoto Ono, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 86 days.

(21) Appl. No.: 16/411,205

(22) Filed: May 14, 2019

(65) Prior Publication Data

US 2019/0268508 A1    Aug. 29, 2019

Related U.S. Application Data

(63) Continuation of application No. PCT/JP2017/032131, filed on Sep. 6, 2017.

(30) Foreign Application Priority Data

Jan. 17, 2017  (JP) ............................. JP2017-006131

(51) Int. Cl.
*A61B 1/00* (2006.01)
*A61B 1/045* (2006.01)
(Continued)

(52) U.S. Cl.
CPC .......... *A61B 1/00009* (2013.01); *A61B 1/045* (2013.01); *H04N 5/2173* (2013.01);
(Continued)

(58) Field of Classification Search
USPC .................................................. 348/65, 302
See application file for complete search history.

(56) References Cited

U.S. PATENT DOCUMENTS

2008/0136948 A1\* 6/2008 Muramatsu ............ H04N 5/335
348/294
2014/0320618 A1\* 10/2014 Akahane ............ H04N 5/23203
348/65

FOREIGN PATENT DOCUMENTS

EP          2950524 A1    12/2015
JP      2009-239337 A    10/2009
(Continued)

OTHER PUBLICATIONS

International Search Report dated Dec. 5, 2017 issued in PCT/JP2017/032131.

*Primary Examiner* — Clifford Hilaire
(74) *Attorney, Agent, or Firm* — Scully, Scott, Murphy & Presser, P.C.

(57) ABSTRACT

An image pickup apparatus includes: a first sample hold circuit configured to sample-hold an image pickup signal; a second sample hold circuit configured to sample-hold a reference voltage signal; an output selection circuit configured to switchingly select one of the image pickup signal inputted from the first sample hold circuit and the reference voltage signal and output a selected signal as an image pickup output; and a timing generator configured to control a timing of the switching selection of the output selection circuit; wherein the timing generator decides the timing of the switching selection so that the reference voltage signal is transmitted in one pixel transmission period required for transmission of the image pickup signal of one pixel, and the reference voltage signal is transmitted once every time the image pickup signal of each of a plurality of pixels is transmitted.

6 Claims, 7 Drawing Sheets

(51) Int. Cl.
*H04N 5/217* (2011.01)
*H04N 5/374* (2011.01)
*H04N 5/378* (2011.01)
*H04N 7/18* (2006.01)

(52) U.S. Cl.
CPC ............ *H04N 5/374* (2013.01); *H04N 5/378* (2013.01); *H04N 7/183* (2013.01); *A61B 1/00043* (2013.01)

(56) References Cited

FOREIGN PATENT DOCUMENTS

| | | |
|---|---|---|
| JP | 2010-232804 A | 10/2010 |
| JP | 5596888 B1 | 9/2014 |
| WO | WO 2014/115390 A1 | 7/2014 |

* cited by examiner

IMAGE PICKUP APPARATUS AND ENDOSCOPE SYSTEM

CROSS REFERENCE TO RELATED APPLICATION

This application is a continuation application of PCT/JP2017/032131 filed on Sep. 6, 2017 and claims benefit of Japanese Application No. 2017-006131 filed in Japan on Jan. 17, 2017, the entire contents of which are incorporated herein by this reference.

BACKGROUND OF THE INVENTION

1. Field of the Invention

The present invention relates to an image pickup apparatus adopting a high-resolution image pickup device, and an endoscope system.

2. Description of the Related Art

Conventionally, image pickup apparatuses adopting a CMOS (complementary metal oxide semiconductor) type image sensor (hereinafter referred to as a CMOS sensor) as an image pickup device have been widely used. An image pickup apparatus using a CMOS sensor is provided with a noise removal circuit for removing fixed pattern noise that occurs according to transistor variation and reset noise that occurs when pixels are reset. The noise removal circuit performs a correlated double sampling process of performing reading twice, reading of a noise component and reading of a signal component including the noise component to remove the noise component based on a difference between the read signals.

Endoscopes including such an image pickup apparatus and are used for diagnosis, treatment using a treatment instrument and the like in a medical field and the like are widely used. In an endoscope system, an image pickup device such as a CMOS image sensor is provided at a distal end of an endoscope insertion portion, and it is possible to display an observation image picked up using the image sensor on a TV monitor by a video processor.

In such an endoscope system, it is necessary to transmit an image pickup signal from the image sensor disposed on the distal end of the insertion portion to the video processor through a relatively long cable. Moreover, it is necessary to decrease a diameter of the cable of the endoscope in order to make the cable easy to bend and easy to insert into a lumen, which is disadvantageous in a point of transmission loss. Therefore, even if noise of an image sensor output has been removed, there is a high possibility that noise is mixed into an image pickup signal during transmission, and image quality of an observation image may deteriorate.

Therefore, Japanese Patent No. 5596888 proposes an image pickup apparatus that transmits a reference voltage signal and an image pickup signal of each pixel in time division in order to remove such noise during transmission, noise due to variation of a power source voltage for driving an image pickup portion, and the like. By using the technique of Japanese Patent No. 5596888, it is possible to acquire an image pickup signal that is a transmitted signal from which a noise component has been removed.

SUMMARY OF THE INVENTION

An image pickup apparatus according to one aspect of the present invention is an image pickup apparatus transmitting an image pickup output generated by multiplexing a reference voltage signal and an image pickup signal in time division, the image pickup apparatus including: a first sample hold circuit configured to sample-hold the image pickup signal; a second sample hold circuit configured to sample-hold the reference voltage signal; an output selection circuit configured to switchingly select one of the image pickup signal inputted from the first sample hold circuit and the reference voltage signal inputted from the second sample hold circuit and output a selected signal as the image pickup output; and a timing generator configured to control a timing of the switching selection of the output selection circuit; wherein the timing generator decides the timing of the switching selection so that the reference voltage signal is transmitted in one pixel transmission period required for transmission of the image pickup signal of one pixel, and the reference voltage signal is transmitted once every time the image pickup signal of each of a plurality of pixels is transmitted.

An endoscope system according to one aspect of the present invention is provided with: an endoscope including the image pickup apparatus according to claim 1; a transmission cable configured to transmit the image pickup output outputted from the image pickup apparatus; a signal processing circuit configured to remove common mode noise included in the image pickup signal based on the reference voltage signal and the image pickup signal included in the image pickup output transmitted via the transmission cable; and a processor configured to generate an observation image by signal processing for the image pickup signal from which the noise is removed by the signal processing circuit.

DETAILED DESCRIPTION OF THE PREFERRED EMBODIMENT

An embodiment of the present invention will be described in detail below with reference to drawings.

Figure 1:
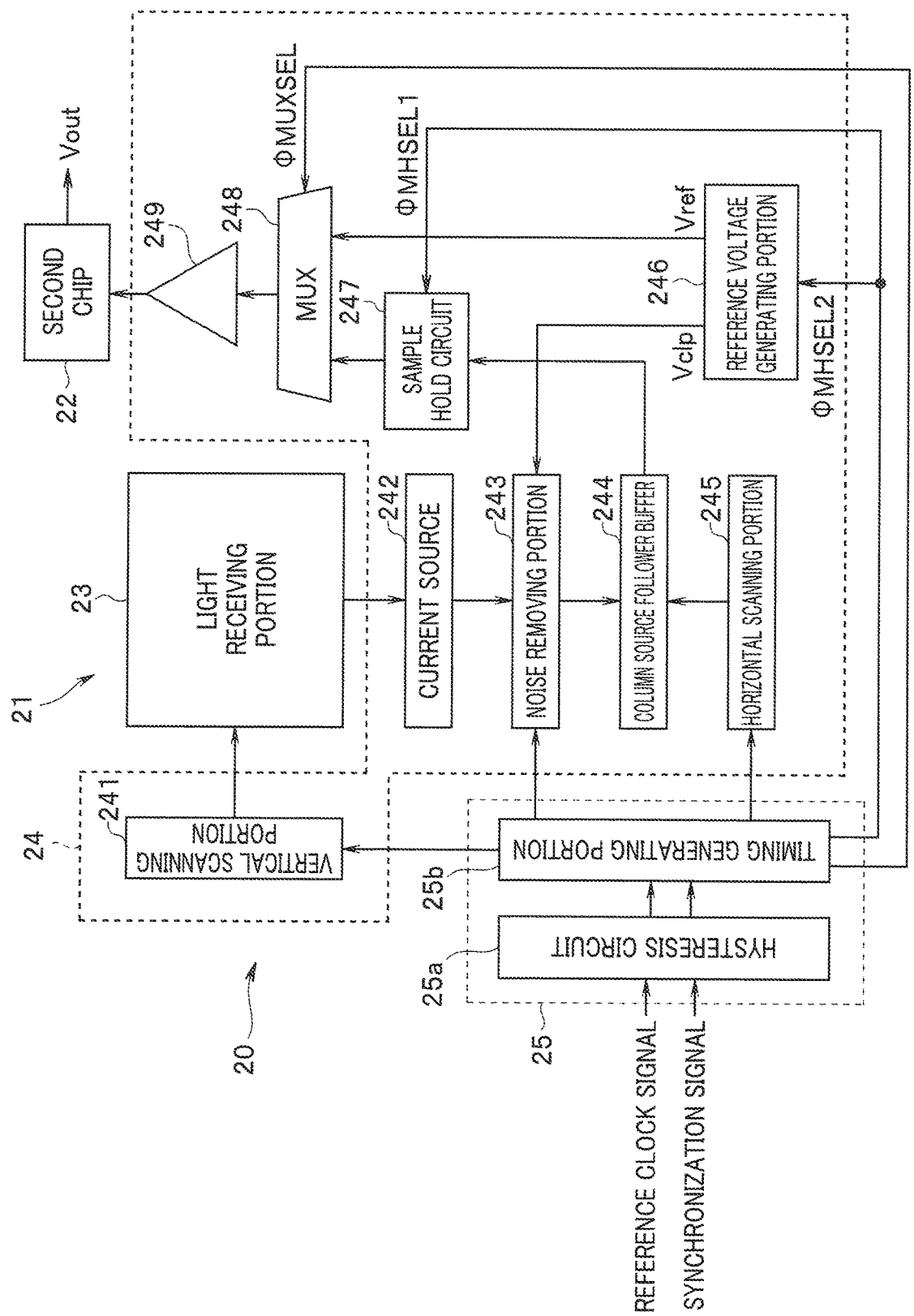
FIG. 1 is a block diagram showing an image pickup apparatus according to one embodiment of the present invention.
Figure 2:
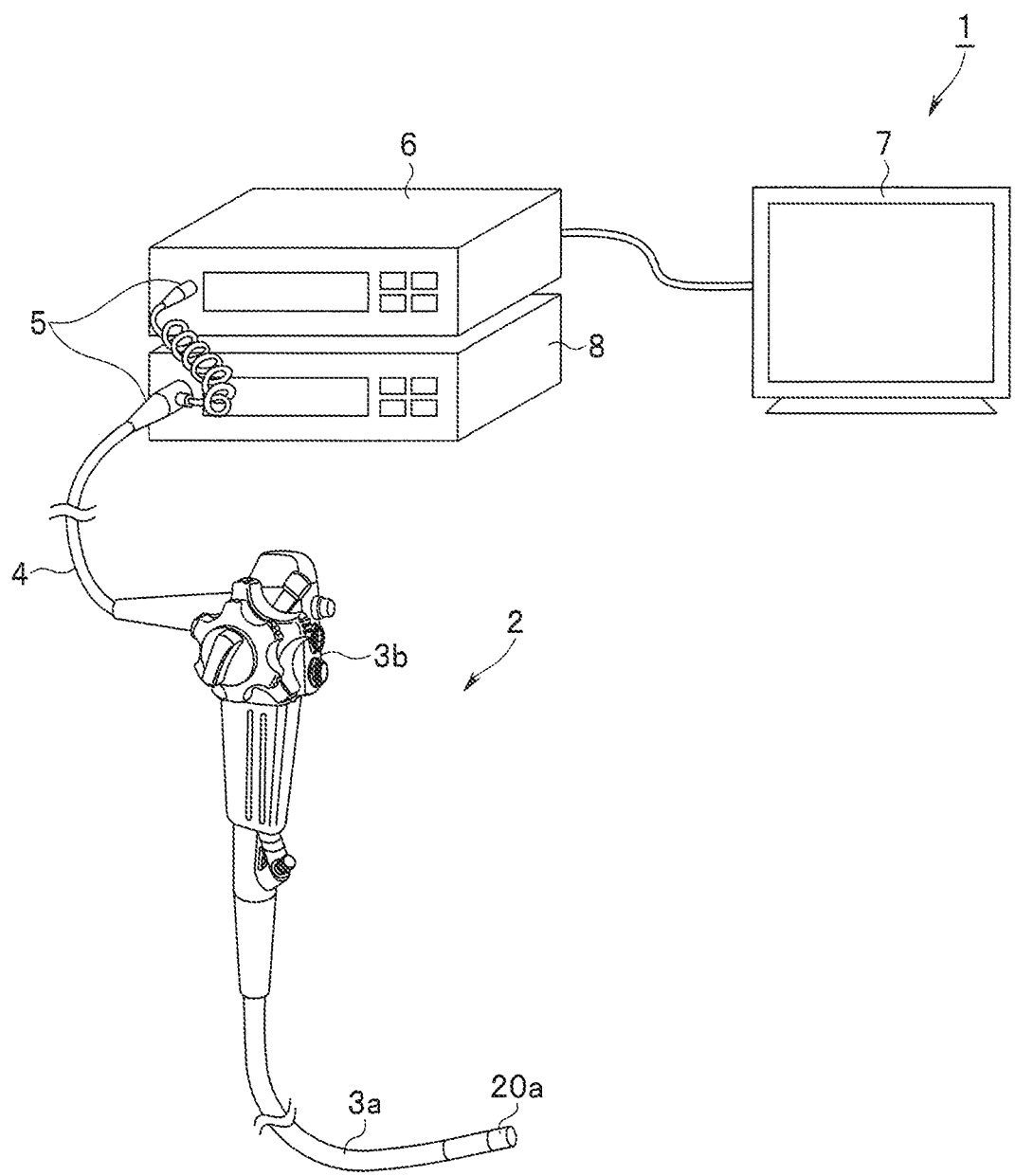
FIG. 2 is an explanatory diagram showing an example of an endoscope system including an endoscope in which the image pickup apparatus of FIG. 1 is included.
Figure 3:
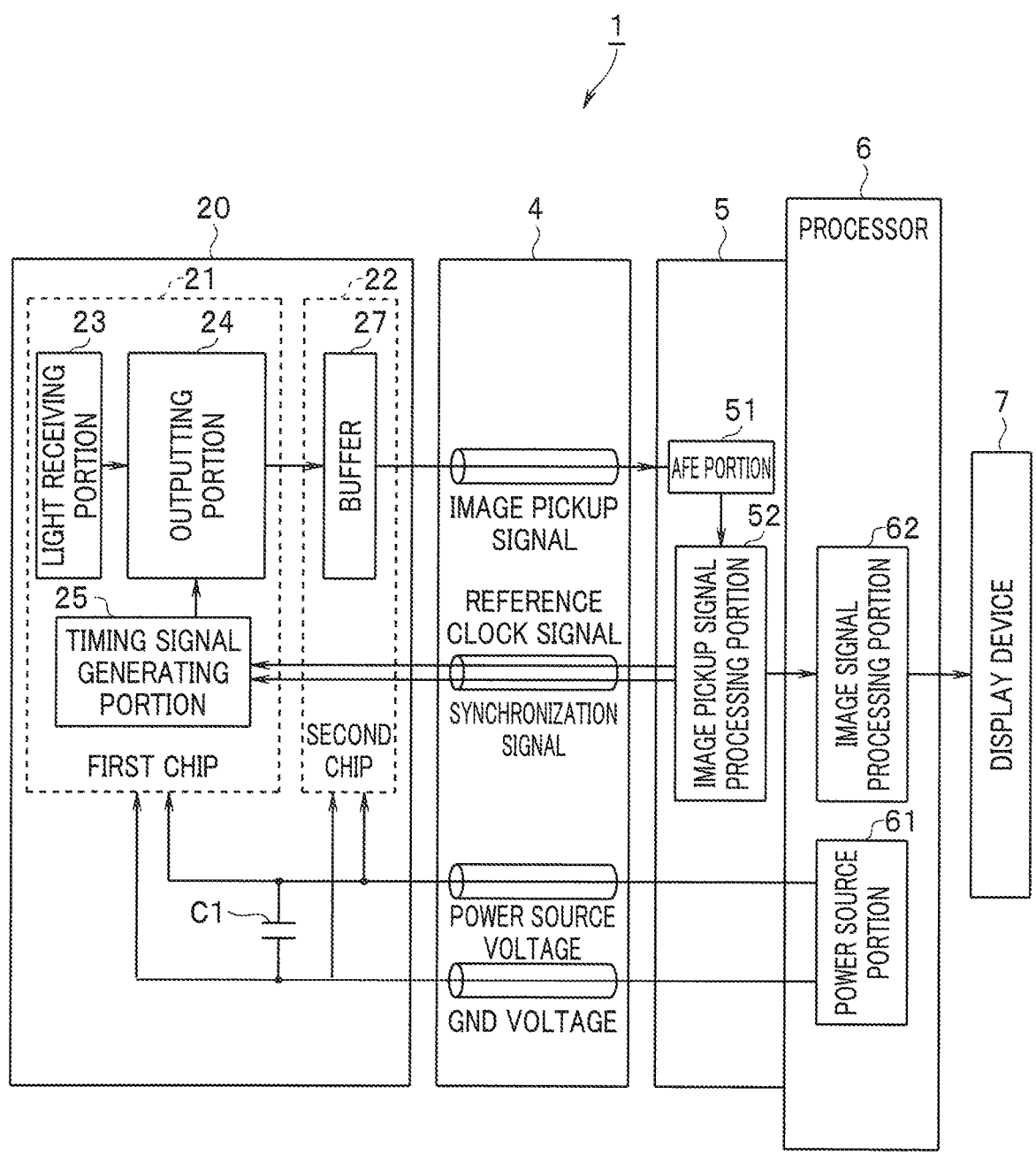
FIG. 3 is a block diagram showing functions of main components of the endoscope system.
Figure 4:
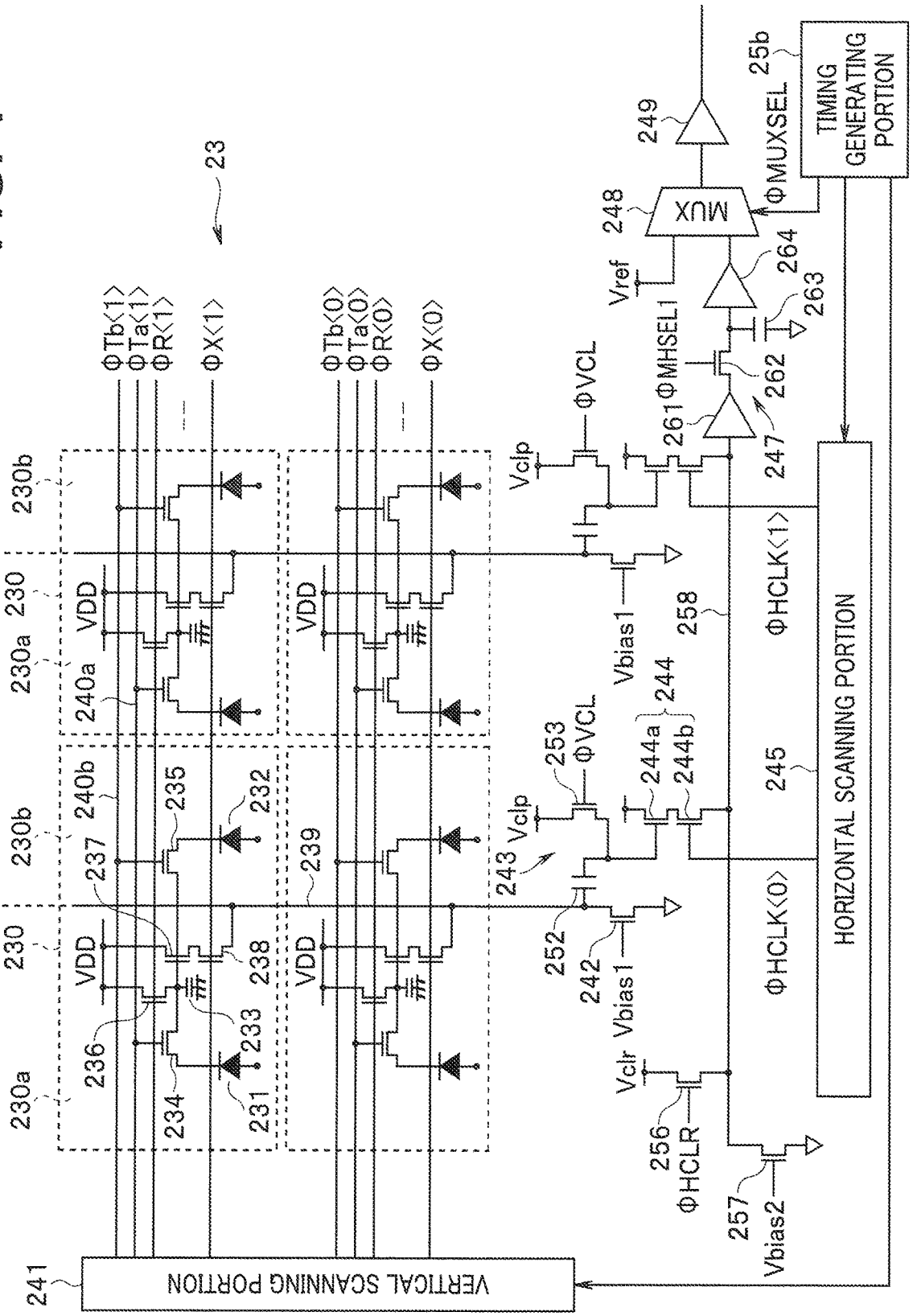
FIG. 4 is a circuit diagram specifically showing a configuration of a main part of the image pickup apparatus.

FIG. 1 is a block diagram showing an image pickup apparatus according to one embodiment of the present invention. FIG. 2 is an explanatory diagram showing an example of an endoscope system including an endoscope in which the image pickup apparatus of FIG. 1 is included. FIG. 3 is a block diagram showing functions of main components of the endoscope system. FIG. 4 is a circuit diagram specifically showing a configuration of a main part of the image pickup apparatus. The present embodiment adopts a scheme in which, at the time of transmitting an image pickup signal, a reference voltage signal and the image signal are transmitted in time division. In this case, in the present embodiment, an amount of transmission is reduced by making an average transmission cycle of the reference voltage signal longer than an average transmission cycle of the image pickup signal of each pixel.

First, a configuration of the endoscope system will be described with reference to FIG. 2. In FIG. 2, an endoscope system 1 is provided with an endoscope 2, a processor 6, a display device 7 and a light source device 8. The endoscope 2 has an elongated insertion portion 3a insertable into a lumen and the like, and an image pickup portion 20 configured with a CMOS sensor or the like is disposed in a distal end portion 20a of the insertion portion 3a. An operation portion 3b is provided on a proximal end side of the insertion portion 3a of the endoscope 2, and a transmission cable 4 is extended from the operation portion 3b. The transmission cable 4 is provided with a connector portion 5 on an extension end portion, the connector portion 5 being configured with a light source connector and an electrical cable extending from a side portion of the light source connector. The transmission cable 4 is detachably connected to the light source device 8 via the light source connector and detachably connected to the processor 6 via the electrical cable. Between the image pickup portion 20 and the processor 6, transmission of signals is performed via the transmission cable 4 and the connector portion 5.

The light source device 8 emits illumination light. The illumination light is led to the distal end portion 20a via an optical fiber inserted in the connector portion 5, the transmission cable 4 and the insertion portion 3a of the endoscope 2 and radiated to an object from an illumination window provided on the distal end portion 20a, the illumination window being not shown. Return light from the object by the radiation of the illumination light is incident onto an image pickup surface of the image pickup portion 20. The image pickup portion 20 photoelectrically converts an incident object optical image of the subject and outputs an image pickup output including an image pickup signal based on accumulated charge.

The image pickup output is transmitted to the processor 6 via the transmission cable 4 and the connector portion 5. The processor 6 generates an observation image (an endoscopic image) of the object by signal processing of the inputted image pickup output and outputs the observation image to the display device 7. In this way, the object observation image is displayed on a display screen of the display device 7.

Each component of the endoscope system 1 will be further described with reference to FIG. 3.

The processor 6 has a power source portion 61. The power source portion 61 generates power for driving each portion and transmits a power source voltage and a ground (GND) voltage by the connector portion 5, the transmission cable 4 and two power source lines inserted in the insertion portion 3a. The image pickup portion 20 is provided with a capacitor C1 for power source voltage stabilization, between the two power source lines. The image pickup portion 20 is provided with a first chip 21 and a second chip 22, and power is supplied to the chips 21 and 22 by the two power source lines.

The connector portion 5 is provided with an image pickup signal processing portion 52. The image pickup signal processing portion 52 can be configured, for example, with an FPGA (field programmable gate array), and the image pickup signal processing portion 52 generates a reference clock signal to be a reference of an operation of each component portion of the endoscope 2 and a synchronization signal. The reference clock signal and the synchronization signal are transmitted to the image pickup portion 20 via the transmission cable 4.

The first chip 21 of the image pickup portion 20 has a light receiving portion 23. The light receiving portion 23 includes pixels arranged in a matrix. On the light receiving portion 23, the pixels are configured corresponding to intersections between a plurality of row selection lines that are horizontally wired and a plurality of vertical transfer lines that are vertically wired, as described later. Charge corresponding to an object optical image is accumulated in each pixel of the light receiving portion 23. Each pixel outputs a pixel signal (an image pickup signal) of a pixel value corresponding to the accumulated charge.

When the reference clock signal and a synchronization signal are given, a timing signal generating portion 25 generates a timing signal for reading out each pixel signal and supplies the timing signal to an outputting portion 24. The outputting portion 24 reads out the pixel signal from each pixel based on the timing signal. In the present embodiment, the outputting portion 24 multiplexes the read-out pixel signal and the reference voltage signal in time division to output an image pickup output, as described later.

The second chip 22 of the image pickup portion 20 includes a buffer 27 having a function of, when the image pickup output is given from the outputting portion 24 of the first chip 21, transmitting only an AC component of the image pickup output to the processor 6. The image pickup portion 20 supplies the image pickup output from the buffer 27 to the connector portion 5 via the transmission cable 4.

In the connector portion 5, an analog front end (AFE) portion 51 is configured. The AFE portion 51 performs a correlated double sampling process for the inputted image pickup output to remove noise. In other words, the AFE portion 51 takes out an image pickup signal from which noise has been removed, from the image pickup output by differential processing between an image pickup signal component and a reference voltage signal component included in the image pickup output. After amplifying the image pickup signal from which the noise has been removed, the AFE portion 51 converts the image pickup signal to a digital signal by analog/digital conversion processing and outputs the digital signal. The digital image pickup signal is supplied to the image pickup signal processing portion 52. For the digital image pickup signal for which signal processing such as noise removal has been performed, the image pickup signal processing portion 52 performs various kinds of signal processing for transmitting the digital image pickup signal to a subsequent-stage circuit to output a video signal.

The digital video signal from the image pickup signal processing portion 52 is supplied to an image signal processing portion 62 of the processor 6 via the electrical cable. The image signal processing portion 62 performs various kinds of processing such as color signal processing for generating a color signal, gamma correction processing, electronic zoom processing and white balance (W/B) processing for the inputted video signal, converts the video signal to a display format appropriate for the display device 7 and outputs the video signal to the display device 7. In this way, an object image (an observation image) picked up by the image pickup portion 20 is displayed on the display screen of the display device 7.

Next, a configuration of the outputting portion 24 mounted on the first chip 21 of FIG. 3 will be further described with reference to FIG. 1.

The timing signal generating portion 25 is configured with a hysteresis circuit 25a and a timing generating portion 25b. The hysteresis circuit 25a performs waveform shaping of a reference clock signal and a synchronization signal that have been long-distance transmitted through the transmission cable 4. The reference clock signal and the synchronization signal that have been waveform-shaped by the hysteresis circuit 25a are supplied to the timing generating portion 25b.

The timing generating portion 25b generates various kinds of drive signals (φTa, φTb, φR, φX, φVCL, φHCLR, φHCLK, φMUXSEL, φMHSEL1 and φMHSEL2) (see FIG. 4) for driving the outputting portion 24 based on the reference clock signal and the synchronization signal that have been waveform-shaped. The timing generating portion 25b gives the drive signals φTa, φTb, φR and φX to a vertical scanning portion 241, gives the drive signals φVCL, φHCLR and φHCLK to a horizontal scanning portion 245, gives the drive signal φMUXSEL to a multiplexer (MUX) 248, gives the drive signal φMHSEL1 to a sample hold circuit 247, and gives the drive signal φMHSEL2 to a reference voltage generating portion 246.

The vertical scanning portion 241 drives the respective pixels of the light receiving portion 23 for each row based on the drive signals supplied from the timing generating portion 25b (φT, φR and φX). The horizontal scanning portion 245 drives the respective pixels of the light receiving portion 23 based on the drive signals (φVCL, φHCLR and φHCLK) supplied from the timing generating portion 25b.

The reference voltage generating portion 246 performs sampling of a reference voltage based on a sampling pulse φMHSEL2, generates a clamp voltage Vclp and gives the clamp voltage Vclp to a noise removing portion 243. The reference voltage generating portion 246 also generates a reference voltage signal of a voltage Vref and gives the reference voltage signal to the MUX 248.

Each pixel of the light receiving portion 23 is driven by a constant current source 242 to output a pixel signal to the noise removing portion 243. The noise removing portion 243 removes fixed pattern noise and reset noise from each pixel signal using the clamp voltage Vclp as described later. A column source follower buffer 244 is driven by the horizontal scanning portion 245 to output the pixel signal from which noise has been removed by the noise removing portion 243, to the sample hold circuit 247. The sample hold circuit 247 as a first sample hold circuit performs sampling of the pixel signal based on a sampling pulse φMHSEL1 and outputs the pixel signal to the MUX 248.

The MUX 248 as an output selecting portion is supplied with the pixel signal from the sample hold circuit 247 and supplied with the reference voltage signal from the reference voltage generating portion 246, and the MUX 248 selects each of the two inputs at a predetermined timing based on a selection signal φMUXSEL and outputs each of the two inputs to a buffer 249. In the present embodiment, the MUX 248 performs selection between the two inputs so that an average reference voltage signal selection cycle is longer in comparison with an average pixel signal selection cycle. For example, the MUX 248 selects the reference voltage signal for a period required to transmit one pixel signal (hereinafter referred to as one pixel transmission period) for every plurality of image signals. Consequently, in the present embodiment, it is possible to improve a transmission rate in comparison with a case of alternately selecting and transmitting a pixel signal of one pixel and a reference voltage signal for one pixel transmission period.

The buffer 249 amplifies an inputted image pickup output and supplies the image pickup output to the second chip 22.

Next, the image pickup portion 20 will be further described with reference to FIG. 4.

In FIG. 4, the light receiving portion 23 is provided with respective pixels corresponding to respective intersections between a plurality of row selection lines 240a and a plurality of vertical transfer lines 239 and respective intersections between a plurality of row selection lines 240b and the plurality of vertical transfer lines 239. Photoelectric conversion elements (photodiodes) 231 correspond to pixels 230a of odd columns of the light receiving portion 23, and photoelectric conversion elements (photodiodes) 232 correspond to pixels 230b of even columns of the light receiving portion 23. In the photoelectric conversion elements 231 and 232, charges corresponding to lights received in light receiving areas of the pixels 230a and 230b are accumulated, respectively.

In the present embodiment, an example is shown which corresponds to a so-called two-pixel sharing in which each of unit pixels (unit cells) 230 is configured with a pixel 230a of an odd column and a pixel 230b of an even column, and one unit pixel 230 is driven by a common vertical transfer line 239, common transistors 236 to 238 and a common floating diffusion (FD) 233. Consequently, it is possible to reduce a size of the light receiving portion 23 relative to the number of pixels of the light receiving portion 23 in a horizontal direction. Configurations of the respective unit pixels 230 are mutually the same.

In other words, the example of FIG. 4 shows an example of a multi-pixel sharing sensor in which one pixel is configured with one photoelectric conversion element 231 or 232, the FD 233 and the like are shared by a plurality of pixels such that the unit pixels 230 having mutually same configurations are configured, and the light receiving portion 23 includes the unit pixels 230 arranged in a matrix. In the example of FIG. 4, the light receiving portion 23 has pixels of 2 m columns (m is a natural number) corresponding to the unit pixels 230 of m columns. Though FIG. 4 shows an example in which each unit pixel 230 is configured with two pixels, each unit pixel 230 may be configured with three or more pixels.

The vertical scanning portion 241 generates a row selection pulse φTa<N>, a row selection pulse φTb<N>, a reset pulse φR<N> and an output pulse φX<N> for driving pixels of the N-th row (N=0, 1, 2, . . . ) based on the drive signals (φT, φR and φX) supplied from the timing generating portion 25b.

Each unit pixel 230 has one common FD 233 for the pixels 230a and 230b, and a drain source path of a transistor 234 is provided on a charge transfer path from the photoelectric conversion element 231 of the pixel 230a of an odd column to the FD 233. Further, a drain source path of a transistor 235 is provided on a charge transfer path from the photoelectric conversion element 232 of the pixel 230a of an even column to the FD 233.

A row selection pulse φTa<N> for selecting pixels of the N-th row is given to a gate of the transistor 234 from the vertical scanning portion 241 via the row selection line 240a. Further, a row selection pulse φTb<N> for selecting pixels of the N-th row is given to a gate of the transistor 235 from the vertical scanning portion 241 via the row selection line 240b.

By the transistor 234 being turned on, charge accumulated in the photoelectric conversion element 231 is transferred to the FD 233 and accumulated. By the transistor 235 being turned on, charge accumulated in the photoelectric conversion element 232 is transferred to the FD 233 and accumulated. The FD 233 can generate a voltage signal according to the accumulated charge.

The FD 233 is connected to a power source terminal VDD via drain source path of the transistor 236. A reset pulse ϕR<N> for resetting the pixels of the N-th row is supplied from the vertical scanning portion 241 to a gate of the transistor 236. By the transistor 236 being turned on, the FD 233 is reset to a predetermined potential.

Between the power source terminal VDD and each vertical transfer line 239, the drain source path of the transistor 237 and a drain source path of the transistor 238 are connected in series. A voltage corresponding to charge accumulated in the FD 233 is supplied to a gate of the transistor 237. The transistor 237 constitutes a source follower and supplies a voltage generated in the FD 233 to a drain of the transistor 238. The output pulse ϕX<N> for transferring the pixel signals of the pixels of the N-th row is supplied to a gate of the transistors 238 from the vertical scanning portion 241. By the transistor 238 being turned on, a voltage corresponding to the charge accumulated in the FD 233, that is, a pixel signal is transferred to the vertical transfer line 239. Note that as described later, a reset pixel signal and a non-reset pixel signal are transferred to the vertical transfer line 239.

Each vertical transfer line 239 is connected to a ground terminal via a drain source path of the transistor 242 which is a constant current source. By a bias voltage Vbias1 being applied to a gate of the transistor 242, the transistor 242 functions as a constant current source. Each pixel is constant-current driven by the transistor 242, and, by the transistor 238 being turned on, a pixel signal is read out to the vertical transfer lines 239.

The vertical transfer lines 239 are connected to a horizontal transfer line 258 via the noise removing portions 243 and the column source follower buffers 244, respectively. The column source follower buffers 244 are controlled by the horizontal scanning portion 245 to transfer pixel signals from the respective vertical transfer lines 239 to the horizontal transfer line 258.

The horizontal scanning portion 245 generates a column selection pulse ϕHCLK<M> for selecting pixel signals from unit pixels 230 of the M-th column <M> (M=0, 1, 2, ..., m−1) of the light receiving portion 23 based on a drive signal (ϕHCLK) supplied from the timing generating portion 25b. Note that it is possible to select pixel signals from the two pixels 230a and 230b included in each unit pixel 230, by each column selection pulse ϕHCLK<M>.

The noise removing portion 243 includes a transfer capacity (an AC coupling capacitor) 252 and a clamp transistor 253. One end of the transfer capacity 252 is connected to the vertical transfer line 239, and the other end is connected to a source of the transistor 253. The clamp voltage Vclp is supplied to a drain of the transistor 253 from the reference voltage generating portion 246, and a clamp pulse ϕVCL is supplied to a gate from the timing generating portion 25b. The transistor 253 is turned on by the clamp pulse ϕVCL, and applies the clamp voltage Vclp to the other end of the transfer capacity 252.

As described later, when a reset pixel signal is supplied to the vertical transfer lines 239, the transistor 253 is on, and the other end of the transfer capacity 252 is clamped to the clamp voltage Vclp.

At a time of no reset, the transistor 253 is off. When the non-reset pixel signal is transferred to the vertical transfer line 239 in this state, a pixel signal from which a noise component at the time of reset has been removed is obtained at the other end of the transfer capacity 252. In this way, the noise removing portion 243 can output the pixel signal from which the noise at the time of reset has been removed.

Since the noise removing portion 243 does not require a capacitor for sampling (a sampling capacity), the capacity of the transfer capacity (the AC coupling capacitor) 252 is only required to have a capacity enough for an input capacity of a transistor 244a. In addition, an area occupied by the noise removing portion 243 on the first chip 21 can be reduced thanks to non-existence of the sampling capacity.

The column source follower buffer 244 is configured with transistors 244a and 244b, and a drain source path of the transistor 244a and a drain source path of the transistor 244b are connected between a power source terminal and the horizontal transfer line 258. The other end of the transfer capacity 252 is connected to a gate of the transistor 244a, and the transistor 244a constituting a source follower supplies a pixel signal supplied to the gate to a drain of the transistor 244b.

A column selection pulse ϕHCLK<M> is supplied to a gate of the transistor 244b from the horizontal scanning portion 245. By the transistor 244b being turned on, a pixel signal from the pixels 230a or the pixels 230b is transferred to the horizontal transfer line 258.

One end of the horizontal transfer line 258 is connected to a ground terminal via a drain source path of a transistor 257, one end of the transistor 257 constituting a constant current source. By a bias voltage Vbias2 being applied to a gate of the transistor 257, the transistor 257 functions as the constant current source. Consequently, by the transistor 244b being turned on, a pixel signal can be read out to the horizontal transfer line 258 from the other end of the transfer capacity 252.

A horizontal reset voltage Vclr is applied to a drain of a horizontal reset transistor 256, and a source is connected to the horizontal transfer line 258. A horizontal reset pulse ϕHCLR is applied to a gate of the horizontal reset transistor 256 from the timing generating portion 25b. By the horizontal reset transistor 256 being turned on in a horizontal reset period, the horizontal transfer line 258 is reset to a predetermined potential.

The other end of the horizontal transfer line 258 is connected to the sample hold circuit 247. The sample hold circuit 247 includes a buffer 261 connected to the horizontal transfer line 258, a transistor 262, a sampling capacity 263 and an operational amplifier 264.

The buffer 261 is given a pixel signal and a noise signal in a horizontal reset period via the horizontal transfer line 258. An output end of the buffer 261 is connected to an input end of the operational amplifier 264 via a drain source path of the transistor 262. The input end of the operational amplifier 264 is connected to a ground terminal via the sampling capacity 263.

A horizontal sampling pulse ϕMHSEL1 is given to a gate of the transistor 262 from the timing generating portion 25b. In an on period of the transistor 262, a signal transferred from the horizontal transfer line 258 via the buffer 261 is accumulated and held in the sampling capacity 263, and supplied to the operational amplifier 264. The operational amplifier 264 amplifies the inputted signals and outputs the signals to the multiplexer (MUX) 248.

As described later, by turning on the transistor 262 in a period other than the horizontal reset period in which pixel signals are transferred to the horizontal transfer line 258, the sample hold circuit 247 performs sampling of a pixel signal and outputs the pixel signal to the MUX 248.

As described above, an image pickup signal from which noise has been removed is transferred to the horizontal transfer line 258. By outputting an image signal while resetting the horizontal transfer line 258 by the horizontal reset transistor 256, it becomes possible to suppress cross talk of image pickup signals in a column direction. Further, by causing the transistor 262 to be in an on state at the time of transferring an image pickup signal after removal of noise and to be in an off state at the time of transferring a noise signal in a horizontal reset period, in the sample hold circuit 247, it becomes possible to output only the image pickup signal after removal of noise to the operational amplifier 264. By the first chip 21 being provided with the sample hold circuit 247, it is possible to halve a bandwidth of a subsequent-stage amplification circuit and suppress a range.

An image pickup signal from which noise has been removed, the image pickup signal being outputted from the sample hold circuit 247, and a reference voltage signal of the reference voltage Vref generated by the reference voltage generating portion 246 are inputted to the multiplexer 248.

Figure 5:
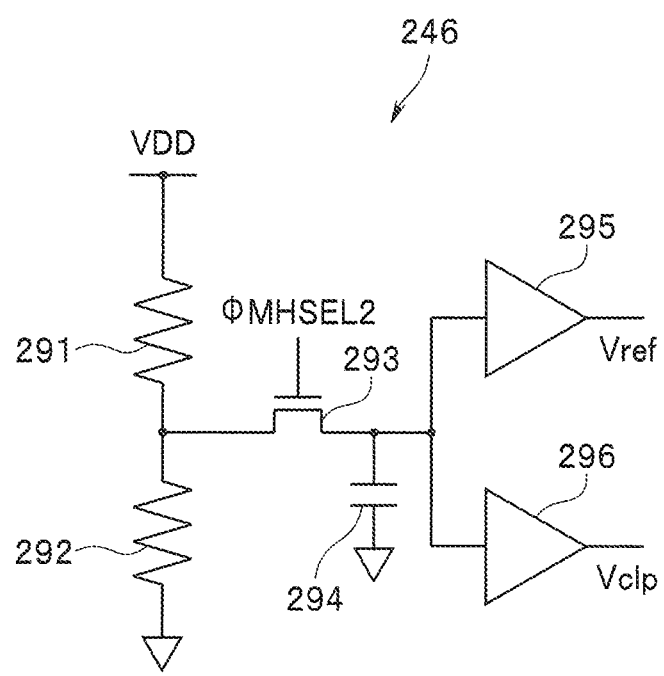
FIG. 5 is a circuit diagram showing an example of a specific configuration of a reference voltage generating portion 246 in FIG. 4.

FIG. 5 is a circuit diagram showing an example of a specific configuration of the reference voltage generating portion 246 in FIG. 1.

The reference voltage generating portion 246 has a resistor divider circuit configured with two resistors 291 and 292 connected in series between a power source terminal VDD and a ground terminal. A connection point between the resistors 291 and 292 is connected to input ends of buffers 295 and 296 via a drain source path of a transistor 293. A sampling pulse φMHSEL2 is given to a gate of the transistor 293 from the timing generating portion. The input ends of the buffers 295 and 296 are connected to the ground terminal via a capacitor 294. A second sample hold circuit is configured with the transistor 293 and the capacitor 294.

At the connection point between the resistors 291 and 292, a predetermined constant voltage divided by the resistors 291 and 292 occurs. When the transistor 293 is turned on by the sampling pulse φMHSEL2, the capacitor 294 is charged by the resistor-divided voltage, and the capacitor 294 gives a predetermined constant voltage to the input ends of the buffers 295 and 296. A stable constant voltage can be obtained by the capacitor 294. The buffers 295 and 296 generate a reference voltage Vref and a clamp voltage Vclp, respectively, based on the constant voltage stabilized by the capacitor 294. As described above, the clamp voltage Vclp is supplied to the drain of the transistor 253, and the reference voltage Vref is supplied to the MUX 248 as a reference voltage signal.

In this way, the reference voltage generating portion 246 simultaneously generates the reference voltage Vref and the clamp voltage Vclp for the noise removing portion 243 based on the power source voltage VDD supplied to the first chip 21. When the clamp voltage Vclp is influenced by a fluctuation of the power source voltage VDD, an image pickup signal from which noise is removed by the noise removing portion 243 that uses the clamp voltage Vclp is also influenced by the fluctuation of the power source voltage VDD. Further, when the power source voltage VDD fluctuates, and the clamp voltage Vclp also fluctuates by influence of the fluctuation, the reference voltage Vref is also influenced by the fluctuation of the power source voltage VDD similarly to the clamp voltage Vclp.

Therefore, by using an image pickup signal and a reference voltage signal, it is possible to remove a fluctuation component that occurs in a power source voltage VDD, from the image pickup signal. Furthermore, in order to remove noise that occurs at the time of transmitting the image pickup signal, the reference voltage signal is also transmitted using a signal line for transmitting the image pickup signal.

The MUX 248 selects between an image pickup signal from the sample hold circuit 247 and a reference voltage signal from the reference voltage generating portion 246 in time division according to the selection signal φMUXSEL supplied from the timing generating portion 25b as a timing controlling portion, and outputs a selected signal as an image pickup output. In the present embodiment, the sample hold circuit 247 performs the selection so that an average reference voltage signal transmission cycle is longer in comparison with an average image pickup signal transmission cycle. The image pickup output from the MUX 248 is supplied to the second chip 22 via the buffer 249.

The buffer 27 of the second chip 22 supplies the image pickup output from the MUX 248 to the AFE portion 51 of the connector portion 5 via the transmission cable 4. The AFE portion 51 uses the image pickup signal and the reference voltage signal to remove noise included in the image pickup signal, by a noise removal process, for example, a correlated double sampling process and outputs the image pickup signal to the image pickup signal processing portion 52.

Into the reference voltage signal, common mode noise similar to noise mixed into the image pickup signal is mixed at the time of transmission via the transmission cable 4. In other words, the reference voltage signal includes not only the fluctuation component of the image pickup signal that occurs in the noise removing portion 243 due to fluctuation of the power source voltage VDD but also a common mode noise component that occurs at the time of transmission of the image pickup output. By the AFE portion 51 performing the noise removal process using the image pickup signal and the reference voltage signal, it is possible to remove the fluctuation component due to the fluctuation of the power source voltage VDD and common mode noise that occurs at the time of transmission, from the image pickup signal.

Figure 6:
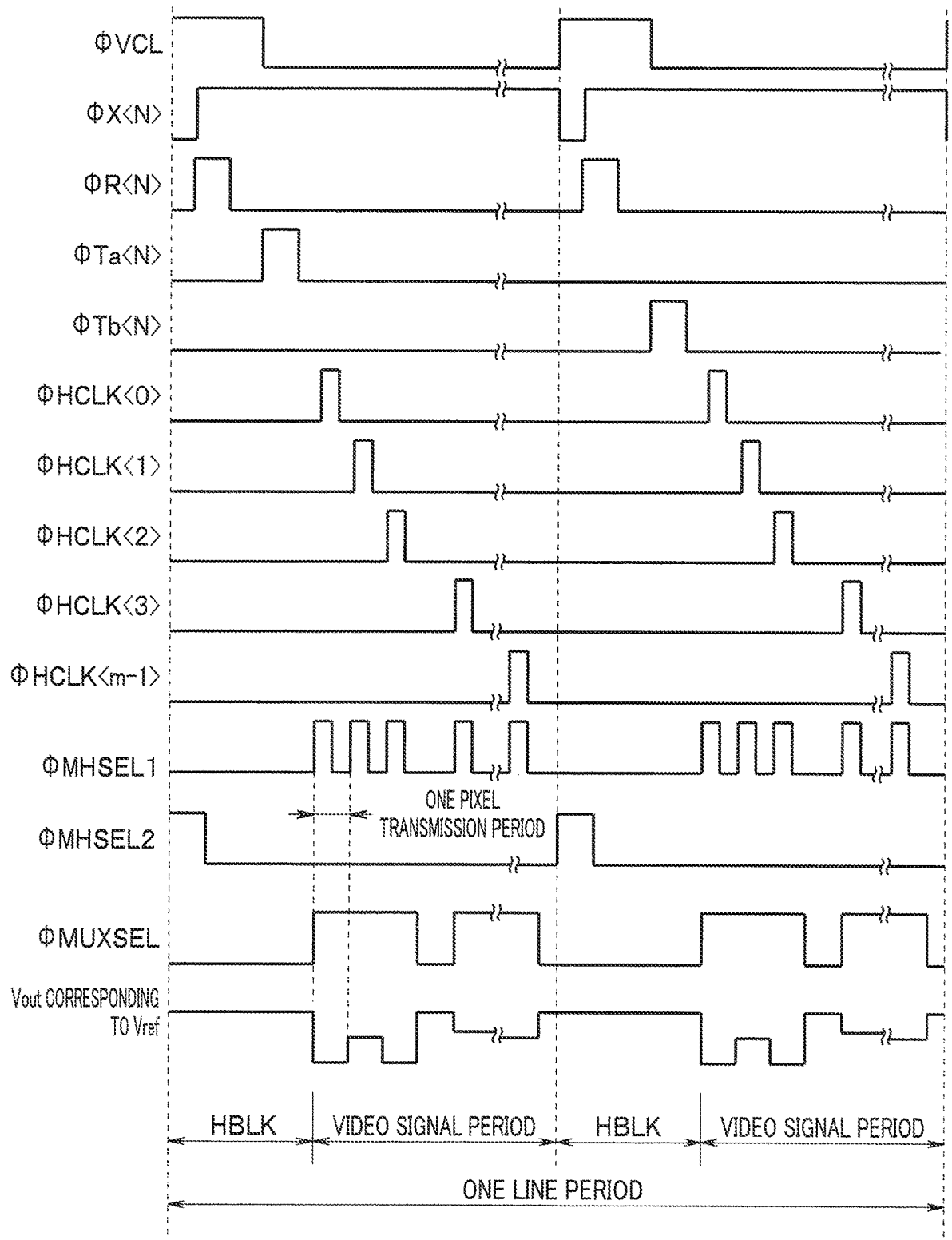
FIG. 6 is a timing chart for illustrating an operation in the embodiment.
Figure 7:
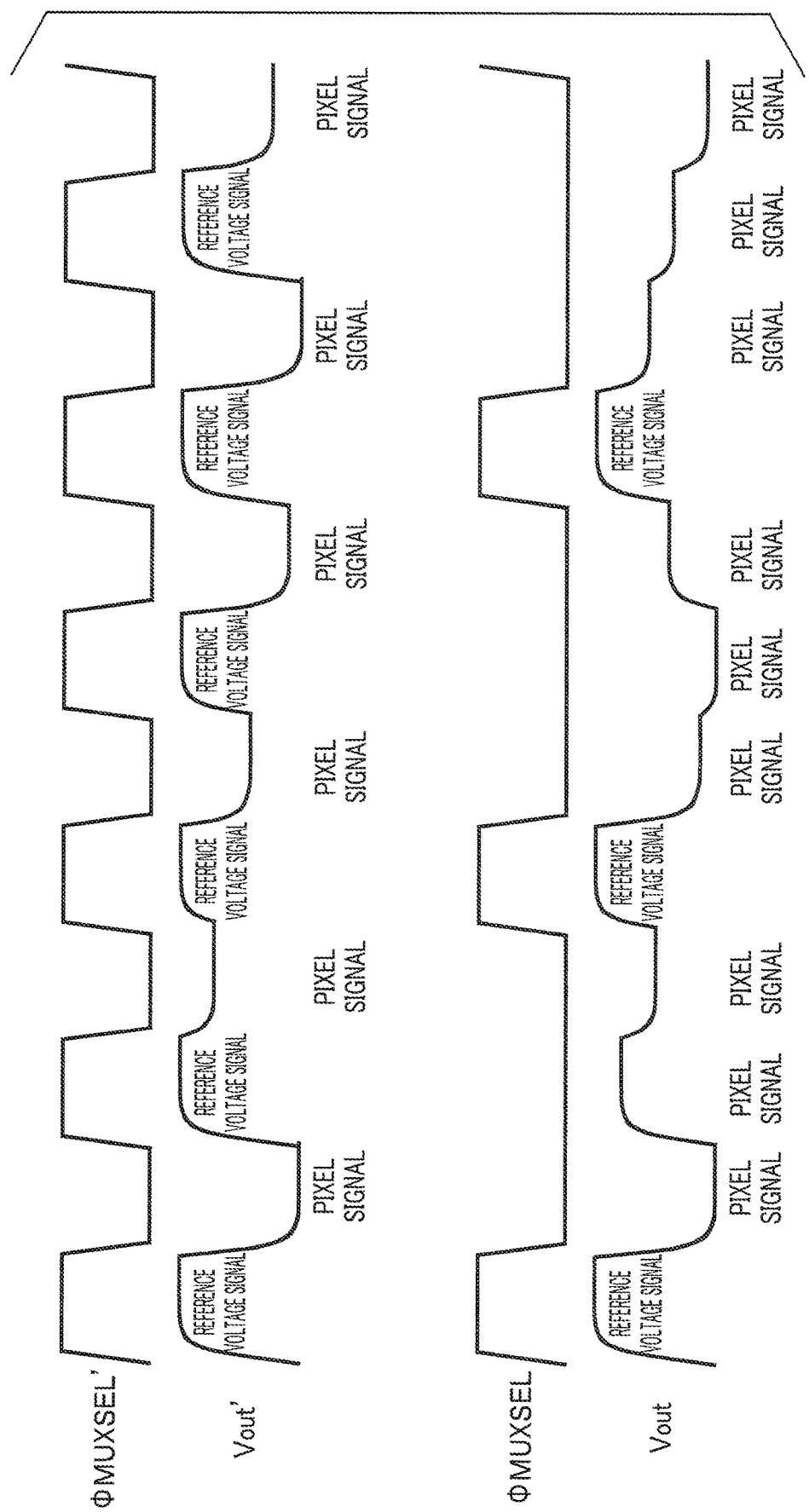
FIG. 7 is a waveform diagram showing an image pickup output outputted from an image pickup portion 20.

Next, an operation of the embodiment configured as described above will be described with reference to FIGS. 6 and 7. FIG. 6 is a timing chart for illustrating the operation in the embodiment. Note that FIG. 6 shows a period from when signals are read out from unit pixels 230 of the n-th row of the light receiving portion 23 until the signals are outputted from the buffer 249. FIG. 7 is a waveform diagram showing an image pickup output outputted from the image pickup portion 20.

The present invention will be described with two-pixel sharing in which vertical transfer lines 239 of m columns are used to read pixel signals of pixels of 2m columns as an example. FIG. 6 shows a period of reading out pixels corresponding to one line (hereinafter referred to as a one line period). A first half period of the one line period (hereinafter referred to as an odd-pixel read-out period) is a read-out period for pixels 230a on left sides of unit pixels 230, and a second half period (hereinafter referred to as an even-pixel read-out period) is a read-out period for pixels 230b on right sides of the unit pixels 230. For each of the unit pixels 230 of a same row, a similar read-out operation is performed. In each of the odd-pixel read-out period and the even-pixel read-out period, a first period is a horizontal blanking period HBLK, and a period following the horizontal blanking period HBLK is a video signal period in which pixels are read out.

When the odd-pixel read-out period or the even-pixel read-out period starts, the horizontal reset pulse φHCLR from the timing generating portion 25b goes to a high level (hereinafter referred to as an H level), the horizontal reset transistor 256 is turned on, and the horizontal blanking period HBLK in which the horizontal transfer line 258 is initialized starts. In the horizontal blanking period HBLK, the clamp pulse φVCL goes to an H level first, and the clamp voltage Vclp from the reference voltage generating portion 246 generated at the timing of an H level of the sampling pulse φMHSEL2 is applied to the other end of the transfer capacity 252 of each column.

In this state, the reset pulse φR<N> goes to an H level, and the FDs 233 are initialized. At the same time, the output pulse φX<N> goes to an H level, and potentials of the FDs 233 are transferred to the respective vertical transfer lines 239 via the transistors 237 and 238.

Next, the reset pulse φR<N> goes to a low level (hereinafter referred to as an L level), and initialization of the FDs 233 ends. Next, the clamp pulse φVCL goes to a low level (hereinafter referred to as an L level). Consequently, clamp of the other end of each transfer capacity 252 is released. Note that the reference voltage generating portion 246 generates a reference voltage signal of the reference voltage Vref at the timing of the H level of the sampling pulse φMHSEL2 and outputs the reference voltage signal to the MUX 248 similarly to the clamp voltage Vclp.

Next, for the pixels 230a on the left sides of the unit pixels 230, the transistors 234 are turned on by the row selection pulse φTa<N>, and charges accumulated in the photoelectric conversion elements 231 are transferred to the FDs 233, and potentials of the FDs 233 are transferred to the vertical transfer lines 239 via the transistors 237 and 238. Consequently, a pixel signal of each pixel 230a is supplied to the transfer capacity 252 connected to the vertical transfer line 239 of each column. A pixel signal (an image pickup signal) from which a noise component has been removed appears at the other end of each transfer capacity 252.

Next, the horizontal reset pulse φHCLR from the timing generating portion 25b goes to an L level, and the horizontal blanking period HBLK ends and transitions to a video signal period. The timing generating portion 25b causes the column selection pulse φHCLK<0> to go to an H level and turns on a transistor 244b corresponding to a vertical transfer line 239 of a zeroth column. Consequently, a pixel signal of a pixel 230a of a unit pixel 230 of the zeroth column is transferred to the horizontal transfer line 258 from the other end of a transfer capacity 252 via the transistors 244a and 244b. By the horizontal sampling pulse φMHSEL1 going to an H level, the pixel signal is sampling-held and supplied to the MUX 248.

Next, after the horizontal reset pulse φHCLR changes from the L level to the H level, and then to the L level, and the horizontal transfer line 258 is reset (not shown), the row selection pulse φHCLK<1> goes to an H level, and a transistor 244b corresponding to a vertical transfer line 239 of a first column is turned on. Consequently, a pixel signal of a pixel 230a of a unit pixel 230 of the first column is transferred to the horizontal transfer line 258 from the other end of a transfer capacity 252 via the transistors 244a and 244b. By the horizontal sampling pulse φMHSEL1 going to the H level, the pixel signal is sampling-held and supplied to the MUX 248.

Similarly, a pixel signal of a pixel 230a of a unit pixel 230 of a second column is transferred to the horizontal transfer line 258 from the other end of a transfer capacity 252 via transistors 244a and 244b, sampling-held by the sample hold circuit 247 and supplied to the MUX 248.

In the present embodiment, as shown by φMUXSEL in FIG. 6, an H-level selection signal φMUXSEL is given to the MUX 248 in a period in which the pixel signals from the pixels 230a of the unit pixels 230 of the zeroth to second columns are outputted, that is, three pixel transmission periods, and the MUX 248 continuously selects and outputs the inputted pixel signals of the three pixels.

In the present embodiment, the timing generating portion 25b outputs an L-level selection signal φMUXSEL in next one pixel transmission period. Consequently, the MUX 248 selects and outputs a reference voltage signal from the reference voltage generating portion 246 in the next pixel transmission period.

In a further next pixel transmission period, the row selection pulse φHCLK<3> goes to an H level, a transistor 244b corresponding to a vertical transfer line 239 of a third column is turned on, and a pixel signal of a pixel 230a of a unit pixel 230 of the third column is transferred to the horizontal transfer line 258 from the other end of a transfer capacity 252 via the transistors 244a and 244b. By the horizontal sampling pulse φMHSEL1 going to the H level, the pixel signals are sampling-held and supplied to the MUX 248. The MUX 248 has been given the H-level selection signal φMUXSEL and outputs the pixel signal of the pixel 230a of the unit pixel 230 of the third column.

After that, similarly, pixel signals from pixels 230a of fourth and fifth columns are read out and outputted. Then, a reference voltage signal for one pixel transmission period is outputted.

In other words, the timing generating portion 25b repeats an operation of outputting the H-level selection signal φMUXSEL through three consecutive pixel transmission periods and outputting the L-level selection signal φMUXSEL in next one pixel transmission period. Consequently, the MUX 248 repeats an operation of, among four pixel transmission periods, outputting pixel signals corresponding to three pixels in the first three pixel transmission periods and outputting a reference voltage signal in the last one pixel transmission period.

When reading of pixel signals from all pixels 230a of unit pixels 230 corresponding to one line ends, the odd-pixel read-out period ends, and the even-pixel read-out period is started. The even-pixel read-out period is different from the odd-pixel read-out period only in a point that, instead of the row selection pulse φTa<N>, an H-level row selection pulse φTb<N> is generated from the vertical scanning portion 241 to read out pixel signals from pixels 230b.

In the even-pixel read-out period, the timing generating portion 25b also repeats the operation of outputting the H-level selection signal φMUXSEL through three consecutive pixel transmission periods and outputting the L-level selection signal φMUXSEL in next one pixel transmission period. Consequently, the MUX 248 repeats an operation of, among four pixel transmission periods, outputting pixel signals corresponding to three pixels in the first three pixel transmission periods and outputting a reference voltage signal in the last one pixel transmission period. The output of the MUX 248 is amplified by the buffer 249 and then given to the second chip 22.

When the vertical scanning portion 241 ends reading of all pixels of the N-th line in the one line period of FIG. 6, the vertical scanning portion 241 performs reading of next (N+1)th row similarly as in FIG. 6. After that, by similar operations, reading of pixel signals from all pixels of the light receiving portion 23 and transmission of image pickup outputs by the transmission cable 4 are performed.

FIG. 7 is a waveform diagram for illustrating an image pickup output Vout from the second chip 22. In FIG. 7, ɸMUXSEL' and Vout' indicate a selection signal given to a multiplexer from a timing generating portion and an image pickup output from a second chip in Japanese Patent No. 5596888, and ɸMUXSEL and Vout indicate a selection signal and an image pickup output in the present embodiment.

As shown in FIG. 7, as for the image pickup output Vout' in the proposal of Japanese Patent No. 5596888, a reference voltage signal and a pixel signal are alternately outputted for each pixel transmission period. In comparison, as for the image pickup output Vout in the present embodiment, a reference voltage signal is transmitted once for every four pixel transmission periods, and a pixel signal is transmitted three times for four pixel transmission periods. In other words, an average pixel signal transmission cycle is (4/3) pixel transmission periods, while an average reference voltage signal transmission cycle is four pixel transmission periods. Thus, the average reference voltage signal transmission period is longer than the average pixel signal transmission period.

Therefore, in the present embodiment, it is possible to improve a transmission rate of an image pickup signal over the proposal of Japanese Patent No. 5596888.

An image pickup output from the image pickup portion 20 is supplied to the AFE portion 51 of the connector portion 5 via the transmission cable 4. The AFE portion 51 obtains, by a correlated double sampling process using a reference voltage signal and an image signal included in the image pickup output, an image pickup signal that is the image pickup output from which common mode transmission noise has been removed.

Thus, in the present embodiment, a pixel signal (an image pickup signal) and a reference voltage signal are time-division multiplexed and outputted. The reference voltage signal includes a fluctuation component of a power source voltage included in the image pickup signal and a common mode transmission noise component included in the image pickup signal. By performing noise removal using the reference voltage signal, noise can be removed from the image pickup signal, and an image of higher quality can be obtained. Further, an average reference voltage signal transmission cycle is set longer than an average image pickup signal transmission cycle, and it is possible to improve a transmission rate of the image pickup signal.

Note that though a unit pixel is configured with two pixels adjoining in a column direction as one set in the embodiment described above, a unit pixel may be configured with two pixels adjoining in a row direction as a set, or a unit pixel may be configured with a plurality of pixels adjoining in the row and column directions as a set. Further, a unit pixel may be configured with one pixel without performing pixel sharing.

The present invention is not limited to the above embodiment as it is, and the components can be modified and embodied within a range not departing from the spirit of the invention at a stage of practicing the invention. Further, various inventions can be formed by appropriately combining a plurality of components disclosed in the above embodiment. For example, some of all the components shown in the embodiment may be deleted. Furthermore, components from different embodiments may be appropriately combined.

What is claimed is:

1. An image pickup apparatus transmitting an image pickup output generated by multiplexing a reference voltage signal and an image pickup signal in time division, the image pickup apparatus comprising:
    a first sample hold circuit configured to sample-hold the image pickup signal;
    a reference voltage generation circuit configured to generate the reference voltage signal;
    an output selection circuit configured to switchingly select one of the image pickup signal inputted from the first sample hold circuit and the reference voltage signal inputted from the second sample hold circuit and output a selected signal as the image pickup output; and
    a timing generator configured to control a timing of the switching selection of the output selection circuit, wherein the timing generator decides the timing of the switching selection so that an average transmission cycle of the reference voltage signal longer than an average transmission cycle of the image pickup signal, wherein the reference voltage signal is transmitted once every time the image pickup signal of each of a plurality of pixels is transmitted.

2. The image pickup apparatus of to claim 1, wherein the reference voltage generation circuit is configured to generate the reference voltage signal using an output of a second sample hold circuit configured to sample hold a power source voltage used for generation of the image pickup signal.

3. The image pickup apparatus of claim 1, further comprising:
    a light receiving element on which unit pixels are arranged in a matrix, each of the unit pixels including a plurality of photoelectric conversion elements in an array, each of the plurality of photoelectric conversion elements comprising a pixel, and each of the unit pixels being configured to transfer pixel signals obtained by the plurality of photoelectric conversion elements in time division via a common signal line; and
    vertical and horizontal scanning circuits configured to generate a scan signal, read out the pixel signals from respective pixels included in each of the unit pixels, and supply the pixel signals as image pickup signals to the first sample hold circuit.

4. The image pickup apparatus of claim 3, further comprising a noise removal circuit configured to remove noise included in the pixel signals read out by the vertical and horizontal scanning circuits to obtain the image pickup signals.

5. An endoscope system comprising:
    an endoscope including the image pickup apparatus of claim 1;
    a transmission cable configured to transmit the image pickup output outputted from the image pickup apparatus;
    a signal processing circuit configured to remove common mode noise included in the image pickup signal based on the reference voltage signal and the image pickup signal included in the image pickup output transmitted via the transmission cable; and
    a processor configured to generate an observation image by signal processing for the image pickup signal from which the noise is removed by the signal processing circuit.

6. The image pickup apparatus of claim 1, wherein the timing generator is configured to transmit the reference voltage signal in one pixel transmission period required for transmission of the image pickup signal.

* * * * *